(12) United States Patent
Striggow et al.

(10) Patent No.: US 7,291,599 B2
(45) Date of Patent: Nov. 6, 2007

(54) USE OF INHIBITORS OF ENZYMES HAVING ACTIVITIES OF AMINO PEPTIDASE N AND/OR DIPEPTIDYL PEPTIDASE IV AND OF PHARMACEUTICAL PREPARATIONS THEREOF FOR A THERAPY AND PREVENTION OF CHRONICAL NEURODEGENERATIVE DISEASES

(75) Inventors: Frank Striggow, Gerwisch (DE); Peter Rohnert, Magdeburg (DE); Till Mack, Magdeburg (DE)

(73) Assignee: Keyneurotek AG, Magdeburg (DE)

( * ) Notice: Subject to any disclaimer, the term of this patent is extended or adjusted under 35 U.S.C. 154(b) by 0 days.

(21) Appl. No.: 10/916,176

(22) Filed: Aug. 11, 2004

(65) Prior Publication Data

US 2005/0113310 A1 May 26, 2005

(30) Foreign Application Priority Data

Aug. 12, 2003 (DE) ............................. 103 37 074

(51) Int. Cl.
*A61K 31/40* (2006.01)
*A61K 31/425* (2006.01)
*A61K 38/05* (2006.01)
*A61K 38/08* (2006.01)

(52) U.S. Cl. ...................... 514/14; 514/15; 514/16; 514/17; 514/18; 514/19; 514/114; 514/119; 514/317; 514/326; 514/330; 514/365; 514/400; 514/422; 514/423; 514/576; 514/578; 514/579; 514/665

(58) Field of Classification Search ............... None
See application file for complete search history.

(56) References Cited

U.S. PATENT DOCUMENTS

| 5,543,396 A * | 8/1996 | Powers et al. ............. 514/19 |
| 6,090,786 A * | 7/2000 | Augustyns et al. .......... 514/19 |
| 2003/0148961 A1 | 8/2003 | Heiser et al. |
| 2004/0147434 A1* | 7/2004 | Ansorge et al. ............. 514/12 |

FOREIGN PATENT DOCUMENTS

| DE | 101 00 053 | 8/2002 |
| WO | WO93/07872 | 4/1993 |
| WO | WO95/34538 | 12/1995 |
| WO | WO 01/34594 | 5/2001 |
| WO | WO 01/34594 A1 * | 5/2001 |
| WO | WO 01/54707 | 8/2001 |
| WO | WO 02/053169 | 7/2002 |
| WO | WO 2004/064866 | 5/2004 |

OTHER PUBLICATIONS

The Merck Index Results, Monograph No.: 09842. Title: Ubenimex. 2006.*
Tanaka et al. Anti-arthritic effects of the novel dipeptidyl peptidase IV inhibitors TMC-2A and TSL-225. Immunopharmacology. 1998, vol. 40, pp. 21-26.*
Wu Young—Qian et al "Neuroprotective effects of inhibitors . . . ", Dipeptidyl Aminopeptides in Health and Disease, Hildebrandt et al, eds. Kluwer Academic, NY, 2003.
Kryzhanovskii G.N. et al. "Effects of Intranasally Administered Substance P . . . ", XP 002298708 2003, Abstract of Biulleten Eksperimentalnoi Biologii I Meditsiny, vol. 113, pp. 16-19 (Jan. 1992).
Gabrilovac, Jelka et al., "Expression of CD 13/Amino-peptidase N . . . " Immunology Letters, 2004 vol. 91, pp. 39-47.
Aoyagi Takaaki et al., "Enzymatic Changes In Cerebrospinal Fluid . . . ", Journal of Clinical Biochemistry And Nutrition 1993, vol. 14, pp. 133-139.
Lendeckel Uwe et al., "Synergistic Action of DPIV and APN . . . ", XP001183828 2003 Dipeptidyl Aminopeptidases in Health and Disease, Hildebrandt et al, Kluwer Academic, NY, 2003, pp. 123-131.
Database WPI, XP002298709 2004, Abstract of WO 2004/064866 (Aug. 5, 2004).
International Preliminary Report on Patentability (Chapter II), Dec. 8, 2004.
Mosimann; Clincial Presentation and Differential Diagnosis of Dementia with Lewy Bodies and Parkinson's Disease Dementia: Schweiz Med Forum 2005; 5:891-896.

* cited by examiner

*Primary Examiner*—Jeffrey Edwin Russel
(74) *Attorney, Agent, or Firm*—Hodgson Russ LLP

(57) ABSTRACT

The invention relates to a process for the treatment of neurodegenerative diseases wherein mis-folded proteins accumulate in characteristic lesions and contribute substantially to a pathogenesis and to an inflammatory reaction magnifying the damage, by the isolated or joint effect of inhibitors of the alanyl amino peptidase (APN) and of the dipeptidyl peptidase N (DP IV). Our results show that the application of inhibitors of the above-referenced enzymes or of preparations and dosage forms containing such inhibitors is definitely suitable for a therapy and prevention of dementia diseases and conditions.

18 Claims, 2 Drawing Sheets

Products for the treatment of Morbus Alzheimer presently on the market [1]

| Brand Name / Generic Code | Drug Class | Launch Date | Market Share [in %] | Strengths | Weaknesses |
|---|---|---|---|---|---|
| *Aricept / donepezil | Acetyl cholin esterase inhibitor | 1997 | 72.1 | • Status as a "gold-standard"<br>• Once-a-day dosing<br>• No liver toxicity | • Some mild side-effects including headache, pain, fatigue, nausea, insomnia, etc. |
| *Exelon / rivastigmine | Acetyl cholin esterase inhibitor | 2000 | 17.3 | • More potent inhibitor of AChE in the cortex and hippo-campus<br>• few side effects<br>• No known drug interactions | • Twice-daily dosing regimen<br>• Some patients in clinical trials who received higher doses died |
| *Reminyl / galantamine | Acetyl cholin esterase inhibitor | 2001 | 9.8 | • Dual mechanism of action to maximize cholinergic function | • Conclusive evidence of its potential benefit has not yet been proven) |
| AXURA (Ebixa) /Memantine | NMDA receptor antagonist | 2002 (EU) Phase III (USA) | | • Approved for medium severe AD | • no causal treatment |

Figure 1A

| Drugs in development | | | | | |
|---|---|---|---|---|---|
| Alzhemed | anti-ß-amyloid aggregation compound | Phase II clinical trials | | • potentially disease-modifying treatment | • clinical effectiveness not yet proven |
| Lipitor Atorvastatin | statins (HMG-CoA reductase inhibitors) lipid lowering agent | Phase II clinical trials | | • good safety profile of other broadly used statins <br> • epidemiological evidence that statin users have lower prevalence of AD | • mechanism unknown |
| Ampalex | AMPAkine facilitates Glutamate effect at AMPA receptors | Phase II clinical trials | | • | • effect not yet proven |
| Neo Trofin | neurotrophic agent induces production of neurotrophins | Phase II/III clinical trials | | • | • effect not yet proven |
| | ß-Secretase and γ-Secretase inhibitors | Pre-clinical phase | | • potential for disease modifying activity | • inhibition of physiologically important proteases (notch) <br> • based on ß-amyloid hypothesis alone |

[1] Source: Therapeutic Report Series: The CNS Outlook 2007, Reuters Business Insight, 2002; Nervous Breakdown, a Detailed Analysis of the Neurology Market, UBS Global Equity Research, 2001

Figure 1B

USE OF INHIBITORS OF ENZYMES HAVING ACTIVITIES OF AMINO PEPTIDASE N AND/OR DIPEPTIDYL PEPTIDASE IV AND OF PHARMACEUTICAL PREPARATIONS THEREOF FOR A THERAPY AND PREVENTION OF CHRONICAL NEURODEGENERATIVE DISEASES

The invention relates to the deceleration of the progressive Alzheimer-specific neurodegeneration and, hence, describes improvements of pathophysiological and cognitive parameters by the action of inhibitors of amino peptidase N (APN; E.C. 3.4.11.2.; CD13) and/or of dipeptidyl peptidase IV (DP IV; E.C. 3.4.14.5.; CD26) as the result of the separate, of the simultaneous or, with respect to the time, of the immediately successive application of the respective specific inhibitors of these enzymes or of inhibitors of enzymes having a similar substrate specificity (APN- and/or DP IV-analogous enzyme activity) on the basis of amino acid derivatives, peptides or peptide derivatives.

There are a number of aging-related dementia diseases, of which Alzheimer's dementia plays a particularly important role. In the year 2001, in the United States, Japan and in Western Europe 6.5 million people suffered from this disease. Due to the progressive aging of the population in those "developed" countries, a severe increase of those diseases has to be expected.

There are several hypotheses for the development of Alzheimer's dementia. Most of these hypotheses are based on findings found on patients suffering from Alzheimer's dementia inherited within the family. In general, it is assumed that interferences with the processing of two proteins, i.e. the amyloid precursor protein and the tau-protein, result into an accumulation of characteristic protein deposits, into deficits with respect to the neurotransmission and, finally, to a distraction of nerve cells.

Up to now, therapeutic agents of the type of acetyl choline esterase inhibitors (AChEIs) are approved almost exclusively for a treatment. Since August 2002, the effective agent memantine (AXURA), i.e. an antagonist of the NMDA receptor, is on the market in Germany (Therapeutic Report Series: The CNS Outlook to 2007, Reuter's Business Insight, 2002, see FIG. 1).

AChEIs enhance the concentration of the neurotransmitter acetyl choline and result in slight improvements of the cognitive capabilities and of the activities of the daily life (activities associated with daily living). They have relatively low side effects (gastric and intestinal fields) and are low in toxicity.

By a treatment with AChEIs, the progress of the dementia is decelerated slightly (by 0.5 to 1 year). A causal therapy, however, is not possible. For a treatment of progressive stages of the disease, only memantine is approved. A therapy with said effective agent is based on the assumption that an enhanced activity of the NMDA receptor is involved in the pathologic development of Alzheimer's disease. The substance has a good safety profile (it is prescribed as a medicament treating "cerebral performance interferences" under the trade name "Akatinol" since years). Nothing is known about long term effects on the course of the disease. An influence on the basic disease cannot be expected.

Several effective substances following different principles of action are clinically tested in an early stage (see FIG. 1). It remains to be seen in how far these substances result into symptomatic improvements or a deceleration of the course of the disease.

Particularly high expectations are connected to inhibitory substances of β- or γ-secretase. These substances inhibit the generation of the β-amyloid, i.e. of the main component of neuritic plaques. Due to their unspecific inhibition of proteases, effective substances tested up to now exhibit potential side effects. Moreover, some scientists raise doubts that the generation of β-amyloid is the only cause for the Alzheimer' pathology, since the β-amyloid deposits do not correlate to the degree of severity of said disease and offer no declaration for the formation of tau-bundles (neurofibrillary tangles=NFT).

The drugs available up to now do not allow an effective treatment of Alzheimer's dementia. New therapeutic approaches are, hence, utterly required.

Peptidases, as for example, dipeptidyl peptidase IV and amino peptidase N or similarly acting enzymes are of particular interest for a regulation or modulation, respectively, of interactions between cells, since they are, in part, localized in the plasma membrane of the cells as ectoenzymes, interact with other extracellular structures, activate or inactivate, respectively, peptiderge messenger substances by enzyme-catalyzed hydrolysis, and, hence, are important for a cell-to-cell communication. [Yaron A., et al.: Proline-dependent structural and biological properties of peptides and proteins. Crit. Rev. Biochem. Mol. Biol. 1993; 28: 31-81; Vanhoof G., et al.: Proline motifs in peptides and their biological processing. FASEB J. 1995; 9: 736-744].

It was shown that membrane-allocated peptidases like DP IV or APN play a key role in the process of an activation and clonal expansion of immune cells, in particular of T-lymphocytes. [Fleischer B.: CD26 a surface protease involved in T-cell activation. Immunology Today 1994; 15: 180-184; Lendeckel U. et al.: Role of alanyl aminopeptidase in growth and function of human T cells. International Journal of Molecular Medicine 1999; 4: 17-27; Riemann D. et al.: CD13—not just a marker in leukemia typing. Immunology Today 1999; 20: 83-88]; Several functions of mitogene-stimulated mononuclear cells (MNZ) or of enriched T lymphocytes as, for example DNA-synthesis, production and secretion of immunostimulating cytokines (IL-2, IL-6, IL-12, IFN-γ) and helper functions for B-cells (IgG synthesis and IgM synthesis) may be inhibited in the presence of specific inhibitors of DP IV or of APN [Schön E., et al.: The dipeptidyl peptidase IV, a membrane enzyme involved in the proliferation of T lymphocytes. Biomed. Biochim. Acta 1985; 2: K9-K15; Schön E., et al.: The role of dipeptidyl peptidase IV in human T lymphocyte activation. Inhibitors and antibodies against dipeptidyl peptidase IV suppress lymphocyte proliferation and immunoglobulin synthesis in vitro. Eur. J. Immunol. 1987; 17: 1821-1826; Reinhold D., et al.: Inhibitors of dipeptidyl peptidase IV induce secretion of transforming growth factor β1 in PWM-stimulated PBMNC and T cells. Immunology 1997; 91: 354-360; Lendeckel U., et al.: Induction of the membrane alanyl aminopeptidase gene and surface expression in human T-cells by mitogenic activation. Biochem. J. 1996; 319: 817-823; Kähne T., et al.: Dipeptidyl peptidase IV: A cell surface peptidase involved in regulating T cell growth (Review). Int. J. Mol. Med. 1999; 4: 3-15; Lendeckel U., et al.: Role of alanyl aminopeptidase in growth and function of human T cells (Review). Int. J. Mol. Med. 1999; 4: 17-27].

It is already known that a treatment of autoimmune diseases and transplant rejection may be achieved by an inhibition of dipeptidyl peptidase IV localized on immune cells by means of synthetic inhibitors (see, for example, EP-A 0 764 151; WO 095/29,691; EP-A 0 731 789; EP-A 0 528 858).

The invention is based on the surprising finding that the single or simultaneous effect of inhibitors of the intraneuronal dipeptidyl peptidase IV/DP IV/CD26 or of inhibitors of enzymes having a similar substrate specificity (DP IV-analogous enzyme activity) and/or of inhibitors of amino peptidase N/APN/CD13 or of inhibitors of enzymes having a similar substrate specificity (APN-analogous enzyme activity) may decelerate the formation of neurofibrillar tangles (NFT).

Our invention shows that, for a therapy and for a prevention of particularly neurodegenerative diseases accompanied by the generation of neurofibrillar tangles (NFT), i.e. of so-called tauopathies, the single or simultaneous application of inhibitors of DP IV and of APN or of inhibitors of enzymes having a similar substrate specificity (APN- and/or DP IV-analogous enzyme activity) or of corresponding pharmaceutical preparations and dosage forms thereof is suitable.

FIGS. 1A and 1B are tabular summaries of Morbus Alzheimer treatments that are presently commercially available, or are in testing, respectively.

In detail, the invention is based on the findings that the number of neurofibrillar tangles (NFT) in the hippocampus and in other areas of the cerebrum (i.e. amygdala) is reduced by the administration of inhibitors of dipeptidyl petidase IV or of inhibitors of enzymes having a similar substrate specificity and/or of inhibitors of amino peptidase N or of inhibitors of enzymes having a similar substrate specificity. Particular areas of indication for the use according of the invention are diseases of humans were NFT are in-volved, i.e. so-called tauopathies. These include, particularly, without that the invention is restricted to those diseases: Morbus Alzheimer, Morbus Pick, the progressive su-pranuclear palsy, the corticobasal degeneration and the frontotemporal dementia. Further neurodegenerative diseases where misfolded proteins accumulate in characteristic lesions and considerably contribute to a pathogenesis and, thus to a selective destruction of nerve cells, are Morbus Parkinson, Morbus Huntington and diseases caused by priones (e.g. spongiforme encephalopathia).

Up to now, Parkinson's disease is treated exclusively on the level of the symptoms, as already described for Morbus Alzheimer. A treatment often practically includes a combination of levodopa (precursor of the transmitter of the nerve cells involved) and dopamine agonists. Following such a medication, undesired side effects in the form of dyscinesias (blocking) are often observed. Moreover, after several years, the effect is severely worn out. As also for Morbus Alzheimer, it is true for Parkinson's disease that, up to now, no therapy form is existing which acts on the pathogenesis, i.e. acts on the causes of the disease.

The body reacts on various challenges by an inflammation, i.e. a process provided to remove dangerous agents and their deleterious effects. In the course of neurodegenerative diseases, inflammation is presumably triggered by an abnormal accumulation of misfolded proteins and/or signals of pathologically altered neurons. An altered expression of the factors involved in those inflammatory processes may promote, but also counteract the neurodegenerative disease (Wyss-Coray, T., and Mucke, L.: Inflammation in Neurodegenerative Disease—a double-edged sword. Neuron 2002; 35: 419-432). In view of the fact that an inflammation has also positive, neuroprotective aspects, a control or targeted elimination of the negative aspects seems to be a better therapeutic approach, compared to that one to suppress an inflammation basically.

By a combined inhibition of dipeptidyl peptidase IV and of amino peptidase N, first hints to a positive modulation of an inflammation in reaction to neurodegeneration could be achieved already. In an animal model, the infarct volume was reduced by the combined DP IV/APN inhibition after a focal ischemia (unpublished results). In hippocampal orga-notypical cut cultures, a degeneration of the tissue can be triggered by an inflammation, whereby neurons are destroyed, too. Such a degeneration is dependent on activated microglia which plays a decisive role in inflammatory processes in the cerebrum. Also in theses cases, a degeneration of the nerve tissue could be reduced by a combined inhibition of DP IV/APN, which allows a conclusion on a reduction/modulation of the inflammation. However, the exact mechanism of such a protection is not yet fully understood and is under detailed research presently. Nonetheless, it may be stated that there are clear signs for a modulation of the inflammation reaction in a manner interrupting the progressing, self-perpetuating degeneration of nerve tissue. Thus, degenerative processes remain restricted to their primary causes, and an acceleration/expansion of the degeneration by inflammation is prevented. Such a clear deceleration of the pathogenesis could also result into a clear improvement of the symptoms in patients, particularly in early to intermediate stages of the disease or could retard, respectively, the late stages of the disease, which are characterized by a complete dependency upon personal care, perhaps by years.

The use of DP II and/or APN inhibitors could be considered as a completely new, presumably very effective, optionally cost effective therapy form and a valuable alternative component of existing therapy concepts of the above-referenced diseases, above all in their early stages.

The inhibitors of dipetidyl peptidase IV or inhibitors of enzymes having a similar substrate specificity (DP IV-analogous enzyme activity) and/or the inhibitors of amino peptidase N or inhibitors of enzymes having a similar substrate specificity (APN-analogous enzyme activity) applied according to the invention may be administered in pharmaceutically applicable formulation complexes as inhibitors, substrates, pseudo substrates, inhibitory active peptides and peptide derivatives as well as antibodies to those enzymes. The inhibitors according to the invention are used alone or in combination of more of them, preferably in combination of two of them.

Preferred effectors for DP IV are Xaa-Pro-dipeptides, corresponding derivatives, preferably dipeptide phosphonic acid diaryl esters, dipeptide boronic acids (e.g. Pro-boro-Pro) and their salts, Xaa-Xaa-(Trp)-Pro-(Xaa)n peptides (n=0 to 10), corresponding derivatives and their salts and, respectively amino acid (Xaa)-amides, corresponding derivatives and their salts, wherein Xaa is an α-amino acid/imino acid or an α-amino acid derivative/imino acid derivative, respectively, preferably $N^\epsilon$-4-nitrobenzyl oxycarbonyl-L-lysine, L-proline, L-tryptophane, L-isoleucine, L-valine, and cyclic amines, e.g. pyrrolidine, piperidine, thiazolidine, and their derivatives act as amide structure. Such compounds and their preparation were described in an earlier patent (K. Neubert et al. DD 296075A5). Moreover, as effectors for DP IV, there may be used advantageously tryptophan-1,2,3,4-tetrahydroisochinoline-3-carboxylic acid derivatives (TSL) and (2S,2S',2S")-2-[2'-[2"-amino-3"-(indole-3'"-yl)-1"-oxoprolyl]-1',2',3',4'-tetrahydro-6'8'-dihydroxy-7-methoxyisochinol-3-yl-carbonyl-amino]-4-hydromethyl-5-hydropentanoic acid (TMC-2A). One example of an inhibitor of DP IV used advantageously is Lys[Z (NO$_2$]-thiazolidide, wherein Lys is a L-lysine residue and Z(NO$_2$) is the 4-nitrobenzyl oxycarbonyl group (see also DD-A 296075).

Considered for use as alanyl aminopeptidase (aminopeptidase N, APN) inhibitors are, for example, actinonin, leuhistin, phebestin, amastatin, bestatin, probestin, β-aminothiols, α-aminophosphinic acids, α-amino phosphinic acid derivatives, preferably D-Phe-ψ-PO(OH)—CH$_2$]-Phe-Phe and their salts. Bestatin (Ubenimex), actinonin, probestin, phebestin, RB3014 or leuhistin are preferred inhibitors for alanyl aminopeptidase.

The inhibitors or pharmaceutical compositions containing them are administered simultaneously with k‚own carrier substances. Comprised by the invention are also pharmaceutical preparations comprising two or more of the inhibitors of DP IV or, respectively, of inhibitors of enzymes having DP IV-analogous enzyme activity and/or of APN or, respectively, of inhibitors of enzymes having APN-analogous enzyme activity, in a spatially separated formulation in combination with per se known carrier substances, auxiliary substances and/or additives for a simultaneous or, with respect to the time, immediately successive administration with the aim of a joint effect.

On the one hand, the administration occurs as a topical application in the form of, for example, creams, ointments, pastes, gels, solutions, sprays, liposomes and nanosomes, lotions (agitated mixtures), "pegylated" formulations, degradable (i.e. degradable under physiological conditions) depot matrices, hydrocolloid dressings, plasters, microsponges, prepolymers and similar novel carrier substrates, jet injections and other dermatological bases/vehicles including instillative applications, and on the other hand, as a systemic application for oral, transdermal, intravenous, subcutaneous, intracutaneous, intramuscular use in suitable formulations or in a suitable galenic form.

The inhibitor(s) according to the invention as well as preparations containing one or more of said inhibitors and optionally further components as, for example, further inhibitors as well as pharmaceutically acceptable additives, auxiliary substances or carrier substances are used, as prevention or therapy drugs, in a considerable number of dementia diseases and conditions including a formation of neurofibrillar tangles (NFTs), so called tauopathias, and other diseases exhibiting an abnormal accumulation of proteins.

The invention also relates to a process for the therapy and prevention of neurodegenerative diseases of which the pathogenesis is dependent on an inflammation (see above). As examples, the following diseases may be mentioned: Morbus Alzheimer, Morbus Parkinson, Morbus Huntington, diseases caused by priones and further tauopathias as for example, pick's disease, the progressive supranuclear palsy, the corticobasal degeneration and the frontotemporal dementia. The process comprises the administration of inhibitors of dipeptidyl peptidase IV (DP IV) as well as of inhibitors of enzymes having a similar substrate specificity (DP IV-analogous enzyme activity) and/or of inhibitors of alanyl aminopeptidase (aminopeptidase N, APN) as well as of inhibitors of enzymes having a similar substrate specificity (APN-analogous enzyme activity) to a patient being in need of a treatment for a prevention and/or therapy of the above-referenced diseases or conditions.

In a particularly preferred embodiment of the invention, one inhibitor or several inhibitors of said enzymes or one or several pharmaceutical preparation(s) containing those inhibitors as a single substance or preferably, in combination, is/are administered to a patient suffering from one or several of the diseases or conditions indicated in detail below or being in need of a prevention of said diseases or conditions indicated below, which inhibitors are selected from inhibitors of DP IV and are particularly preferably selected from Xaa-Pro-dipeptides (Xaa=α-amino acid or side chain-protected derivative, respectively), corresponding derivatives, preferably dipeptide phosphonic acid diaryl esters, dipeptide boronic acids (e.g. Pro-boro-Pro) and their salts, Xaa-Xaa-(Trp)-Pro-(Xaa)n peptides (Xaa=α-amino acid, n=0 to 10), corresponding derivatives and their salts, amino acid (Xaa) amides, corresponding derivatives and their salts, wherein Xaa is an α-amino acid or a side chain-protected derivative, respectively, preferably N$^ε$-4-nitrobenzyl oxycarbonyl-L-lysine, L-isoleucine, L-valine, L-tryptophane, L-proline, and cyclic amines as, for example, pyrrolidine, piperidine, thiazolidine and their derivatives act as the amide structure, and/or tryptophane-1,2,3,4-tetrahydroisochinoline-3-carboxylic acid derivatives (TSL) and (2S,2S',2S'')-2-[2'-[2''-amino-3''-(indol-3'''-yl)-1''-oxopropyl]-1',2',3',4'-tetrahydro-6'8'-dihydroxy-7-methoxyisochinol-3-yl-carbonyl-amino]-4-hydromethyl-5-hydropentanoic acid (TMC-2A), and from inhibitors of APN, particularly preferably actinonin, leuhistin, phebestin, amastatin, bestatin, probestin, β-aminothiols, α-amino phosphinic acids, at-amino phosphinic acid derivatives, preferably D-ψ-Phe-PO(OH)CH$_2$)-Phe-Phe, and their salts.

In further preferred embodiments according to the invention, the inhibitors, and optionally their combinations and pharmaceutical preparations containing them, are used in the prevention and therapy of diseases and conditions, respectively, which include the generation of neurofibrillar tangles (NFT) and other abnormal protein accumulations. As an example, there may be mentioned the prevention and therapy of Morbus Alzheimer, of pick's disease, of the progressive supranuclear palsy, of the corticobasal de-generation, of the frontotemporal dementia, of Morbus Parkinson, of Morbus Huntington and of diseases caused by priones.

In processes for the prevention and/or therapy particularly preferred according to the invention, one or more of the above-referenced inhibitor(s) of DP IV and/or APN are applied in a manner that two or more of the inhibitors of DP IV or inhibitors enzymes having a DP IV-analogous enzyme activity, respectively, and/or inhibitors of APN or inhibitors of enzymes having an APN-analogous enzyme activity, respectively, are administered in a spatially separated formulation in combination with per se known carrier substances, auxiliary substances and/or additives; the administration is conducted simultaneously or, with respect to the time, immediately successively with the aim of a joint effect. The administration is a systemic administration for an oral, transdermal, percutaneous, intravenous, subcutaneous, intracutaneous, intramuscular, rectal, vaginal, sublingual application, together with per se known carrier substances, auxiliary substances and/or additives and/or as a topical application in the form of creams, ointments, pastes, gels, solutions, sprays, liposomes or nanosomes, respectively, "pegylated" formulations, degradable depot matrices, lotions (agitated mixtures), hydrocolloid dressings, plasters, microsponges, prepolymers and similar new carrier substrates, jet injections and other dermatological bases/vehicles including an instillative application.

The invention is further explained below by means of the subsequent examples. The examples show preferred embodiments of the invention. However, the invention is not restricted to those preferred embodiments.

EXAMPLES

Transgenic mice expressing, under the control of the mouse prione promoter, the human micro tubulus-associated proteine tau having the mutation P301L developed neurofibrillar tangles (NFT), neurodegeneration and deficits in the motion apparatus, connected to affects in their behavior in an age-dependent manner (Lewis J., McGowan E., Rockwood J., Melrose H., Nacharaju P., Van Slegtenhorst M., Gwinn-Hardy K., Paul Murphy M., Baker M., Yu X., Duff K., Hardy J., Corral A., Lin W. L., Yen S. H., Dickson D. W., Davies P., Hutton M. Neurofibrillary tangles, amyotrophy and progressive motor disturbance in mice expressing mutant (P301L) tau protein. Nat. Genet. 2000, 25(4), 402-405). Hence, they may be considered as a complete model for the pathogenesis of human diseases including the formation of NFT, i.e. the so-called tauopathias.

The genuine mouse cell-line JNPL3 was purchased from the company Taconic, Germantown, USA, in a status crossbred with B6D2F1 hybrides. The hemizygote F1 developed primary symptoms of developing disorders in their movements and behavior after approximately 6 months. The corresponding mice were no longer capable to straddle their extremities as a reaction of escaping when taken up at their tails, but, on the contrary, showed spontaneous cramps of the hind leg muscles. After 10 months, more than 90% of the tau-transgenic mice had difficulties when straightening up, and in hanging tests, the rope offered could be grasped with great difficulties, only. Hence, the clinging to the rope often failed.

On a cellular level, the above observations were correlated with the neuropathological changes the most noticeable of which was the formation of NFT, inter alia, in the marrow of the vertebral column. The NFTs could be detected by an application of congo red and thioflavine-S flourescence microscopy as well as be gallya's dying with silver. Moreover, a somatodendritic, "pre-tangle" tau accumulation could be detected in further regions of the brain, particularly in the entorhinal cortex as well as in the hippocampus.

In order to accelerate the NFT formation also in these areas, six to seven months old transgenic mice were injected with fibrilliar abeta 1-42 into the entorhinal cortex or the hippocampus stereotactically. Such an injection provided for the sound generation of a NFT phathology in the hippocampus or in the amygdala, respectively, of transgenic animals, but not in wild-type animals within 2 to 3 weeks, depending upon the point of injection.

In the course of this term, all animals were administered a combination of inhibitors of DP IV (I-49) and of APN (bestatin hydrochride; actinonin) every 2 to 3 days in a concentration of 5 to 10 mg per kg body weight by i.p. injection. Furthermore, both types of inhibitors, respectively, were tested independently up to a concentration of 50 mg per kg of body weight.

It can be assumed that, as a consequence of the stereotactic injection of fibrillar abeta into the entorhinal cortex of one hemisphere of the cerebrum and into the hippocampus of the contralateral hemisphere of the cerebrum, amyloid fibrilles are existing in the tissue at least 45 days after the injection (Götz J., Chen F., van Dorpe J., Nietsch R. M. Formation of neurofibrillary tangles in P301L tau transgenic mice induced by Abeta 42 fibrils: Science 2001, 293 (5534), 1491-1495.). NFTs are formed, respectively, in cell bodies the axons of which projected to the area of injection, i.e. the hippocampus and the amygdala, respectively.

By the administration of inhibitors of DPP IV as well as of inhibitors of APN, the number of NFTs could significantly be reduced in both areas of the cerebrum. Moreover, by the administration of a combination of both inhibitors, there resulted a better NFT protection than for each of the single inhibitors, which fact demonstrates an effect of the combination of the single inhibitors exceeding the addition of both single effects.

Gallya's-positive NFTs were evaluated as described in the documents of Götz et al. (loc. cit.). In addition, serial frontal cuts of the cerebrum were made, and each fifth cut in the proximity to the injection area was analyzed after a Gallya's dying. Gallya's dying-positive NFT were counted on twenty standardized cuts and were added. Mean value and standard error were calculated for three mice each.

Moreover, the result was also an improvement of the general status of the animals. Deficits in the motion apparatus did not occur or occurred only in such a diminished manner, within the term of observation, that the usual reaction of escaping was hardly affected. In addition, a cowered body position with clenched paws as the sitting position was rarely observed, only. Parameters only indirectly connected to the motion apparatus could be considered to be improved, too. Animals treated with DP IV inhibitors/APN inhibitors did not lose weight, and their cleaning behavior was hardly affected.

Summarizing the results, there could be observed a good correlation between a reduction of a neuropathology, particularly of the NET generation, to the improvement of the overall status of the mice. However, it is assumed that the lack of deficits in their behavior does not depend on, or does only indirectly depend on the reduction of the NET formation in the regions of the cerebrum which were analyzed. A correlation of the abnormal behavior with the NET pathology described above and the accompanying neurodegeneration, in particular in the marrow of the cerebral column and in the main cerebral area (Lewis et al., loc. cit.) can be considered to be highly probable. Hence, also the improvements of the apparent behavior may be based either on a protection of the nerve cells by the combination of defective substances tested or at least on a deceleration of the pathogenesis.

The invention claimed is:

1. A method for the reduction of neurodegenerative lesions caused by the formation of aggregates of mis-folded proteins and for the control and/or modulation of inflammation accelerating such lesions comprising the step of administering to a patient in need thereof an effective amount of a composition comprising:
    a) an inhibitor of dipeptidyl peptidase IV (DP IV) and/or at least one inhibitor of enzymes having a similar substrate specificity (DP IV-analogous enzymatic activity), in combination with:
    b) an inhibitor of alanylaminopeptidase (aminopeptidase N; APN) and/or at least one inhibitor of enzymes having a similar substrate specificity (APN-analogous enzymatic activity);
    wherein the neurodegenerative lesions are reduced, and
        wherein the reduction of neurodegenerative lesions is greater than the additive effect of administering the DP IV inhibitor alone or the APN inhibitor alone.

2. The method of claim 1, wherein the DP IV inhibitor is Lys[Z(NO$_2$)]-thiazolidide, wherein Lys is L-lysine and [Z(NO$_2$)] is 4-nitrobenzyl-oxycarbonyl.

3. The method of claim 1, wherein the composition is administered by a route selected from oral, transdermal, intravenous, subcutaneous, intracutaneous, intramuscular, rectal, vaginal, sublingual and percutaneous.

4. The method of claim 1, wherein the inhibitor of DP IV is an Xaa-Pro-dipeptide (Xaa=α-amino acid or side chain protected derivative) or corresponding derivative selected from dipeptide phosphonic acid diaryl esters and salts thereof, dipeptide boronic acids and salts thereof, or wherein the inhibitor of DP IV is an Xaa-Xaa-(Trp)-Pro-(Xaa)$_n$ peptide (Xaa=α-amino acid, n=0 to 10) or salt thereof, or wherein the inhibitor of DP IV is an Xaa-amide or salt thereof, wherein Xaa is an α-amino acid or a side chain protected derivative and the amide is a cyclic amine.

5. The method of claim 4, wherein the α-amino acid or side chain protected derivative is selected from $N^\epsilon$-4-nitrobenzyloxycarbonyl-L-lysine, L-proline, L-tryptophan, L-isoleucine and L-valine.

6. The method of claim 4, wherein the cyclic amine is selected from pyrrolidine, piperidine and thiazolidine.

7. The method of claim 4, wherein the dipeptide boronic acid is Pro-boro-Pro.

8. The method of claim 1, wherein the DP IV inhibitor is selected from the group consisting of amino acid amides consisting of $N^\epsilon$-4-nitrobenzyloxycarbonyl-L-lysine thiazolidide, pyrrolidide and piperidide and corresponding derivatives selected from 2-cyanothiazolidide, 2-cyanopyrrolidide and 2-cyanopiperidide.

9. The method of claim 1, wherein the APN inhibitor is selected from the group consisting of actinonin, leuhistin, phebestin, amastatin, ubenimex, probestin, ({3-[(1-aminoethyl)(hydroxy)phosphoryl]-2-benzylpropanoyl}amino)-(benzyl)acetic acid, β-aminothiols, α-aminophosphinic acids, and α-aminophosphinic acid derivatives.

10. The method of claim 2, wherein the APN inhibitor is ubenimex.

11. The method of claim 8, wherein the APN inhibitor is ubenimex.

12. The method of claim 3, wherein the APN inhibitor is actinonin.

13. The method of claim 1, wherein the aggregates of mis-folded proteins are in the form of neurofibrillar tangles.

14. The method of claim 4, wherein the DP IV inhibitor is selected from the group consisting of tryptophan-1,2,3,4-tetrahydroisoquinoline-3-carboxylic acid derivatives (TSL) and (2S,2S',2S'')-2-[2'-[2''-amino-3''-(indol-3'''-yl)-1''-oxoprolyl]-1',2',3',4'-tetrahydro-6',8'dihydroxy-7'-methoxyisoquinol-3-yl-carbonyl-amino]-4-hydroxymethyl-5-hyrdoxypentanoic acid (TMC-2A).

15. The method of claim 9, wherein the α-aminophosphinic acid derivatives are selected from the group consisting of D-Phe-ψ[PO(OH)-CH2]-Phe-Phe and salts thereof.

16. The method of claim 1, wherein the patient has Morbus Alzheimer.

17. The method of claim 1, wherein the composition is administered in a form selected from the group consisting of a cream, ointment, paste, gel, solution, spray, liposome or nanosome, pegylated formulation, degradable depot matrix, lotion, hydrocolloid dressing, plaster, microsponge, prepolymer, jet injection, and an instillative application.

18. The method of claim 1, wherein the patient has Morbus Parkinson.

* * * * *